United States Patent [19]
Havemann et al.

[11] Patent Number: 5,631,136
[45] Date of Patent: May 20, 1997

[54] PROCESS FOR THE DETECTION OF COMPLEXED CATHEPSIN G AND α-1-ANTICHYMOTRYPSIN

[75] Inventors: Klaus Havemann, Marburg; Hans-Heinrich Heidtmann, Marburg-Bauerbach, both of Germany

[73] Assignee: Behringwerke Aktiengesellschaft, Marburg, Germany

[21] Appl. No.: 353,342

[22] Filed: Dec. 5, 1994

Related U.S. Application Data

[63] Continuation of Ser. No. 76,214, Jun. 10, 1993, abandoned.

[30] Foreign Application Priority Data

Jun. 13, 1992 [EP] European Pat. Off. .............. 92109994

[51] Int. Cl.$^6$ .................................................. G01N 33/53
[52] U.S. Cl. .................... 435/7.4; 435/7.9; 435/7.92; 435/7.95; 435/971; 435/975; 436/518; 436/524; 436/525; 436/527; 436/529
[58] Field of Search ........................... 435/7.4, 7.9, 7.92, 435/7.95, 971, 975; 436/518, 524, 525, 527, 529

[56] References Cited

U.S. PATENT DOCUMENTS 4,849,353  7/1989  Harpel ........................................ 435/7.4

FOREIGN PATENT DOCUMENTS 0038935  11/1981  European Pat. Off. .

OTHER PUBLICATIONS

"Human Alpha–1–Antichymotrypsin: Purification by Preparative Isoelectric Focusing and Development of the Enzyme Immunoassay," Zuklys, et al., Proceedings of the 2nd Int. Conf. Biochemistry (1988) pp. 89–101 Pick et al.

"Human Plasma Proteinase Inhibitors", Travis et.al., Ann. Rev. Biochem., 52: 655–709 (1983).

"Kinetics of Association of Serine Proteinases with Native and Oxidized α–1–Proteinase Inhibitor and α–1–Antichymotrypsin", K. Beatty et. al., The Journal of Biological Chemistry, 255(9): 3931–3934 (1980).

"The Degradation of Cartilage Proteoglycans by Tissue Proteinases", P.J. Roughley et.al., Biochem. J., 167: 629–637 (1977).

"Microbicidal Mechanisms of Human Granulocytes: Synergistic Effects of Granulocyte Elastase and Myeloperoxidase or Chymotrypsin–Like Cationic Protein", H. Odeberg et. al., Infection and Immunity, 14(6): 1276–1283 (1976).

"Rapid Conversion of Angiotensin I to Angiotensin II Neutrophil and Mast Cell Proteinases", Christopher F. Reilly et. al., The Journal of Biological Chemistry, 257(15):8619–8622 (1982).

Harlow, E, et al. Antibodies: A Laboratory Manual. Cold Spring Harbor, NY: Cold Spring Harbor Laboratory, pp. 53–60, 321–322, 1988.

"Effect of Elastase–like and Chymotrypsin–Like Neutral Proteases From Human Granulocytes on Isolated Clotting Factors", Wilhelm Schmidt et. al., Thrombosis Research, 6:315–326 (1975).

(List continued on next page.)

*Primary Examiner*—Carol A. Spiegel
*Attorney, Agent, or Firm*—Finnegan, Henderson, Farabow, Garrett & Dunner, L.L.P.

[57] ABSTRACT

The present invention relates to a process for determining complexes of α-1-antichymotrypsin and cathepsin G in a sample comprising adsorbing the cathepsin G portion of the complex to a solid phase coated with non-specific binding protein or gelatin, and detecting the α-1 portion of the complex with a detectably labelled anti-α-1-antichymotrypsin antibody. A diagnostic kit comprising the solid phase coated with non-specific binding protein or gelatin and the labelled anti-α-1-antichymotrypsin antibody is also provided.

11 Claims, 2 Drawing Sheets

OTHER PUBLICATIONS

"Assay of Functional Activity of $\alpha_1$-Antichymotrypsin in Plasma", Hans–Heinrich Heidtmann et. al., Clinical Chemistry, 36(12):2077–2081 (1990).

"PMN–Elastase Assay": Enzyme Immunoassay for Human Polymorphonuclear Elastase Complexed with $\alpha_1$-Proteinase Inhibitor, S. Neumann et. al., J. Clin. Chem. Clin. Biochem., 22(10):693–697 (1984).

"Partial Purification and Characterization of a Chymotrypsin–like Enzyme From Human Neutrophil Leucocytes", Andreas Ch. Gerber et.al., Biochimica et Biophysica Acta, 364:103–112 (1974).

"Analysis of the Plasma Elimination Kinetics and Conformational Stabilities of Native, Proteinase–Complexed, and Reactive Site Cleaved Serpins: Comparison of $\alpha_1$-Proteinase Inhibitor, $\alpha_1$-Antichymotrypsin, . . . Angiotensinogen, and Ovalbumin", Alan E. Mast et. al., Biochemistry, 30(6):1723–1730 (1991).

PROCESS FOR THE DETECTION OF COMPLEXED CATHEPSIN G AND α-1-ANTICHYMOTRYPSIN

This application is a continuation of application Ser. No. 08/076,214, filed Jun. 10, 1993, now abandoned.

BACKGROUND OF THE INVENTION

1. Field of the Invention

The invention relates to a process for the detection of complexes of cathepsin G and α-1-antichymotrypsin in body fluids. Furthermore, the invention relates to a diagnostic kit to accomplish this process.

2. Background Art

α-1-antichymotrypsin is a 68-kDa glycoprotein and belongs to the "serpin" family (serine proteinase inhibitors) of proteinase inhibitors in plasma (Journal of Medicine 16: 101–128 (1985); Annual Review of Biochemistry 52: 655–709 (1983)). It is mainly synthesized in the liver, but can be produced by various tissues. The concentration of α-1-antichymotrypsin which is an acute-phase reactant in plasma can drastically increase within hours after injury. It inhibits serine proteinases of chymotrypsin-like specificity. Cathepsin G from neutrophiles is a primary enzyme targeted by α-1-antichymotrypsin. The association rate of α-1-antichymotrypsin for chymotrypsin is too slow to be of biological importance (Journal of Biological Chemistry 255: 3931–3934 (1980)).

Although the interrelationship of α-1-antichymotrypsin and cathepsin G is well established, the physiological role of the system is not known. The several proposed functions of cathepsin G are connective tissue turnover (Biochemical Journal 167: 629–237 (1977)) microbe elimination (Infection and Immunity 14: 1276–1283 (1976)), angiotensin-II generation (Journal of Biological Chemistry 257: 8619–8622 (1982)), turnover of clotting (Thrombocyte Research 6: 315–326 (1975)) and complement factors.

Detection of deficiencies of some other serine proteinase inhibitors homologous to α-1-antichymotrypsin has helped to explain their biological function. However, immunological measurements of α-1-antichymotrypsin fail to detect total α-1-antichymotrypsin deficiency in patients despite intensive screening. Patients with α-1-antichymotrypsin concentrations ≦50% of normal—either heterozygotes for an autosomal dominant trait or acquired by liver impairment—appear to be predisposed to lung and liver disease but no clear cause—effect conclusions can be drawn thus far. Functional impairment of α-1-antichymotrypsin could not be assessed in complex biological fluids such as plasma, because no proteinases are known which react exclusively with α-1-antichymotrypsin. This was, however, achieved by an immunoassay by which active α-1-antichymotrypsin could be specifically measured in plasma (Clinical Chemistry 36: 2077–2081 (1990)).

However, for several applications the measurement of complexes of cathepsin G and α-1-antichymotrypsin in nanomolar concentrations would be desirable in order to recognize disease states with an increased turnover of cathepsin G or α-1-antichymotrypsin. While a sensitive sandwich ELISA (Enzyme Linked Immunosorbent Assay) has been described for the analogous system of human leukocyte elastase and its primary plasma inhibitor, α-1-proteinase inhibitor (J. Clin. Chem. Clin. Biochem. 22: 693–697 (1984); EP-0 038 935), no such assay is available for complexes of cathepsin G and α-1-antichymotrypsin because of the strong avidity of cathepsin G to solid surfaces which prevented the application of cathepsin in such a classic sandwich ELISA.

The task of this invention is therefore to provide an assay for the specific identification of complexes of cathepsin G and α-1-antichymotrypsin in body fluids.

SUMMARY OF THE INVENTION

The solution of this task is a process for the detection of complexes of α-1-antichymotrypsin and cathepsin G in a sample comprising (a) coating the surface of a protein adsorbent with a coating agent, (b) applying the sample containing said complexes to the coated surface, (c) detecting the adsorbed complexes by detecting the α-1-antichymotrypsin with a detecting agent.

DESCRIPTION OF THE PREFERRED EMBODIMENTS

Figure 1:
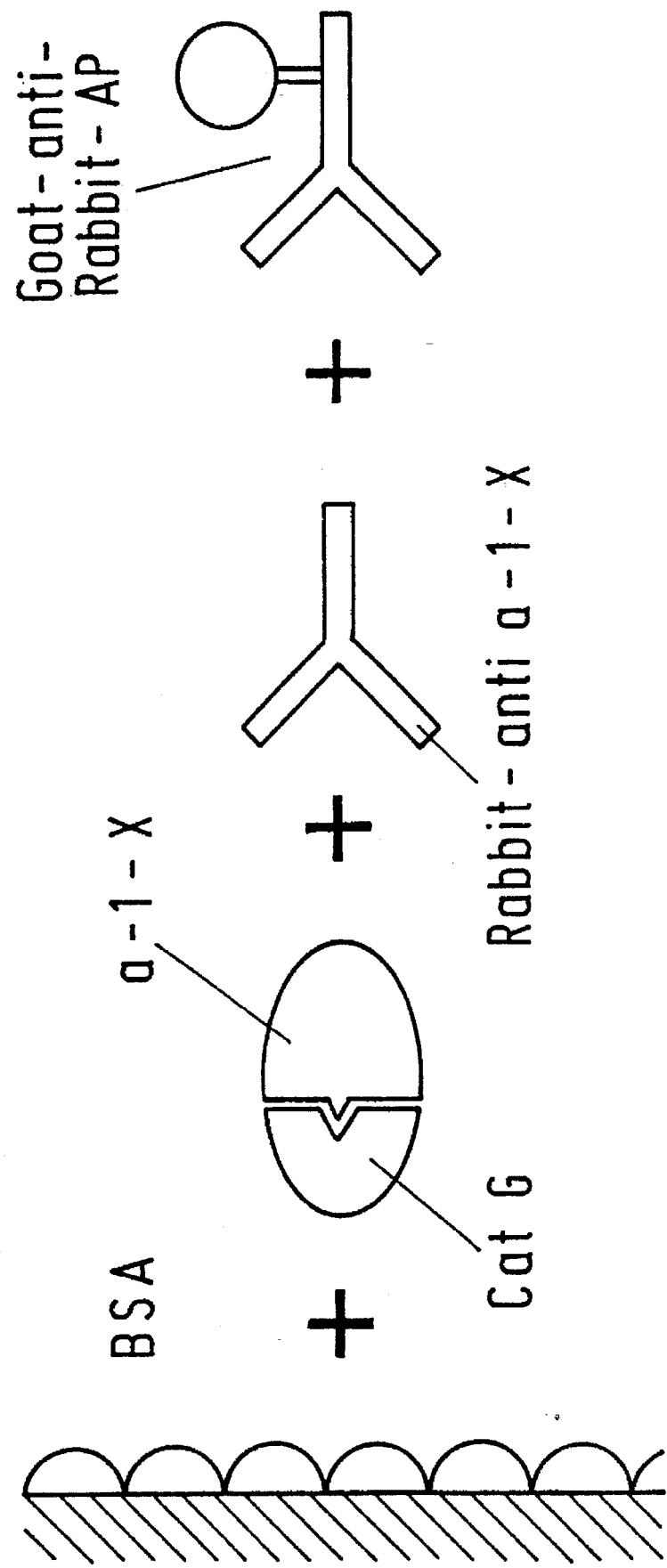
FIG. 1 describes the basic principle of the instant process for complexed α-1-antichymotrypsin detection.

This process makes it possible to detect complexes of cathepsin G and α-1-antichymotrypsin in any sample such as body fluids and supernatants of cell cultures. According to the invention, samples can be taken from blood, plasma, serum, urine, synovial fluid or cerebrospinal fluid. In samples of bronchial lavage fluids of M. Boeck patients elevated concentrations of the complex are found. The assay takes advantage of the high avidity of cathepsin G to coated surfaces of a protein adsorbent. Such surfaces might be selected from material known to those skilled in the art like polystyrene, gold, silica, polyacrylamide or glass. The surface may be formed as microtitration plates, ELISA tubes, latex beads, micro-beads or fleeces.

The coating agent with which the surfaces are saturated are preferably proteins or gelatine; more preferably bovine serum albumin and ovalbumin are used.

The complexes are adsorbed directly by their cathepsin G moiety and can then be quantified with a detecting agent. Such detecting agents are preferably antibodies specific for α-1-antichymotrypsin which either can be labeled or unlabeled. When the antibody is labeled, it is preferably labeled to a radioactive isotope like $I_{125}$, $P_{32}$ or $C_{14}$, or it may be biotinylated or linked to an enzyme. In case the antibody is biotinylated, it is subsequently detected by the well known avidin-biotin system. In case the antibody is linked to an enzyme, the adsorbent activity is followed by the subsequent conversion of a suited substrate. As preferred enzymes, horseradish peroxidase in combination with the substrate o-phenylenediamine or tetramethyl diaminobiphenyl dihydrochloride or alkaline phosphatase in combination with the substrate 4-nitrophenyl phosphate is used. The antibody may also be labeled by coupling with a chemiluminescent or fluorescent agent.

In a preferred embodiment of the invention the detecting agent consists of two antibodies whereby the first antibody which is specific for anti-α-1-antichymotrypsin is subsequently detected by a second antibody. The use of two antibodies as detecting agent leads to an enhancement of the sensitivity of the assay. In case a second antibody is used, the first antibody needs not to be labeled. It is known that any labeling procedure may lead to a partial inactivation of an antibody. This disadvantage is avoided. The second antibody is either labeled by a radioactive isotope like $I_{125}$, $P_{32}$ or $C_{14}$, by an appropriate enzyme or is biotinylated. In the latter case the detection step is then performed with the well-known avidin-biotin system. The antibody is preferably linked to alkaline phosphatase and the suited substrate is 4-nitrophenylphosphate in this case. The antibody may also be labeled by coupling with a chemiluminescent or fluorescent agent.

Protein coated beads may be applied for turbidimetric or nephelometric determinations wherein part of the particles are coated with anti-α-1-antichymotrypsin antibodies.

The inventive process has the advantage that it is very specific for a complex of cathepsin G and α-1-antichymotrypsin. To demonstrate the specificity, cathepsin G was replaced by chymotrypsin and human leukocyte elastase. In neither case absorbance values exceeding those of the corresponding normal plasma could be obtained.

Chymotrypsin is known to form complexes with α-1-antichymotrypsin, although at a rate far slower than cathepsin G. It is therefore not considered a primary physiological target proteinase of α-1-antichymotrypsin. Chymotrypsin has a pI of 8. It did not adhere to the microtiter wells under the given circumstances, and hence no α-1-antichymotrypsin was retained.

Human leukocyte elastase is contained in the same granules as cathepsin G. It does not form complexes with α-1-antichymotrypsin. Since it is also a basic protein with a pI of 10 it was taken care to exclude any non-specific interaction with α-1-antichymotrypsin. No interference was detected. Cathepsin G, when inactivated by diisopropyl fluorophosphate (DFP), was also unable to create any increased absorbance reading. This indicates that specific binding to the inhibitor via the reactive site, not unspecific adherence of the inhibitor to the enzyme is responsible for the retained α-1-antichymotrypsin in the inventive process.

The inventive process is different from known sandwich ELISA for the detection of proteinase inhibitors complexed to human proteinases. The strong avidity of cathepsin G to solid surfaces prevented the application of cathepsin G in such classic sandwich ELISA due to non-specific binding. Attempts to overcome this binding, like addition of 1 Mol/L NaCl, interfered strongly with antibody binding. These serious problems are the reason why, until today, no process has been disclosed for the detection of complexes of cathepsin G and α-1-antichymotrypsin.

The inventive process is superior to known sandwich ELISA.

The strong binding of cathepsin G was exploited by omitting the first antibody of any ELISA scheme known in the art. Complexes of cathepsin G and α-1-antichymotrypsin adhered to the surface of mictrotiter plates even when they were coated with albumin and TWEEN 20 (polysorbate), while free α-1-antichymotrypsin did not bind under these conditions. Bound complexes were then detected immunologically with specific antibodies to α-1-antichymotrypsin.

The strong binding of cathepsin G is due to its basic pI of 10, associated with high arginine content (Biochim. Biophys. Acta 364: 103–112 (1974)), whereas α-1-antichymotrypsin, with a pI of 5, does not adhere to the coated surface.

The calibration series in the process was designed for complex concentrations up to 14 nMol/L. This range was chosen because it covered the values obtained in the preliminary measurement of several plasma specimens from critically ill patients. Since normal plasma which was definitely free of complexes (true sample blank) was not available, calibration specimens were prepared by adding known amounts of preformed complexes to plasma pooled from 50 healthy donors. Thus, the results from the calibration curve can only express concentration of complexes in addition to whatever is contained in normal plasma. The concentration of complexes prevalent in the normal plasma had to be estimated by extrapolation of the calibration curve to the reagent blank. The values of the individual normal plasma specimens showed a constantly low level with a narrow standard deviation, making the identification of pathologically increased values rather easy. Whether the absorbance of the normal plasma above the reagent blank was due to a steady-state complex concentration or background noise, cannot be determined. However, for practical purposes this can be neglected, since it was less than a 10 % increment of the total range of the assay. This is in good agreement with the finding that proteinase-complexed α-1-antichymotrypsin is rapidly cleared from the circulation (Biochemistry 30(6): 1723–1730 (1991)).

In the following, the inventive process is described in more detail.

The basic priciple of the assay for complexed α-1-antichymotrypsin is shown in FIG. 1. Mictrotiter plates were coated with albumin and TWEEN 20 (polysorbate) in order to prevent non-specific binding of plasma proteins. α-1-antichymotrypsin complexed with cathepsin G adhered to this surface via the cathepsin G moiety. Immobilized α-1-antichymotrypsin was then detected with antiserum to α-1-antichymotrypsin.

The following reagents were used: Lyophilized, pure α-1-antichymotrypsin (ARTS, Athens, GA, USA) was reconstituted with H20 to a concentration of 1 g/L in 50 mmol/L Tris buffer, pH 8.0, containing 150 mmol of NaCl per liter. α-1-antichymotrypsin activity was determined by evaluating complex formation in 8% SDS-polyacryl gel electrophoresis with addition of increasing amounts of cathepsin G. The preparation was fully active as judged by assessing its complex formation with cathepsin G. Cathepsin G (EC 2.3.21.20), at 3.3 g/L in a buffer containing 50 mmol of acetic acid and 500 mmol of NaCl per liter, pH 5.5, and human leukocyte elastase (EC 3.4.21.11), at 2.0 g/L in the same buffer, were used. Rabbit antiserum against human α-1-antichymotrypsin was from DAKO, Copenhagen, Denmark. Goat antiserum against rabbit immunoglobulin coupled to alkaline phosphatase (EC 3.1.3.1) was from Jackson Immunoresearch Laboratories, Westgrove, Pa. Bovine serum albumine (RIA-grade), TWEEN 20 (polysorbate), and bovine chymotrypsin (EC 3.4.21.1) were from Sigma Chemical, St. Louis, Mo., USA. 4-Nitrophenyl phosphate (disodiumhexahydrate), and DMSO were from Merck, Darm-stadt, FRG. Succinyl-alanyl-alanyl-prolyl-phenylalanyl-paranitroanilide was from SERVA, Heidelberg, FRG. Heparin sodium (Liquemin$^R$) was from Hoffmann-La Roche, Grenzach-Wyhlen, FRG.

Cooke$^R$ 96 well mictrotiter plates were from Greiner, N ürtingen, FRG. A Titertek Multiscan photometer (Flow, Helsinki, Finland) was used to measure the absorbance of the microtiter plates. For blood samples, syringes (Monovette$^R$ "Coagulation 5 mL", Sarstedt, Nümbrecht, FRG) were used containing 0.5 mL of 106 mmol/L sodium citrate solution as an anticoagulant.

Cathepsin G activity was monitored with the chromogenic substrate succinyl-alanyl-alanyl-prolyl-phenylalanylparanitroanilide described above. To inactivate cathepsin G with di-isopropyl fluorophosphate (DFP), the enzyme was incubated at a concentration of 0.33 g/L in the presence of 10 mmol/L of DFP in a buffer containing 0.2 M/L Tris and 0.5 mol/L NaCl, pH 8.0. After 15 min, no residual activity could be detected. To prepare complexes of cathepsin G with α-1-antichymotrypsin, the proteinase, at a concentration of 0.033 g/l, was incubated with a twofold molar excess of active α-1-antichymotrypsin in a buffer containing 0.2 mol/L Tris and 0.5 mol/L NaCl, pH 8.0, for 10 min at room temperature.

After this time, no residual proteinase activity could be detected.

Specimen Experiments: Venous or arterial blood was collected into citrate-containing syringes, taking care to prevent potential infection. Plasma was obtained by centrifugation at 2000 g for 10 min, and frozen immediately. Specimens were stored in aliquots at −20° C. for up to 1 month without apparent changes. Repeated thawing up to 4 times did not influence the results. Storage at 4° C. over 24 hours led to 40% loss of signal strength. Centrifugation could be delayed for up to 2 hours without any changes in the final values. Arterial and venous blood specimens, taken from the same patient at the same time, gave identical results.

Figure 2:
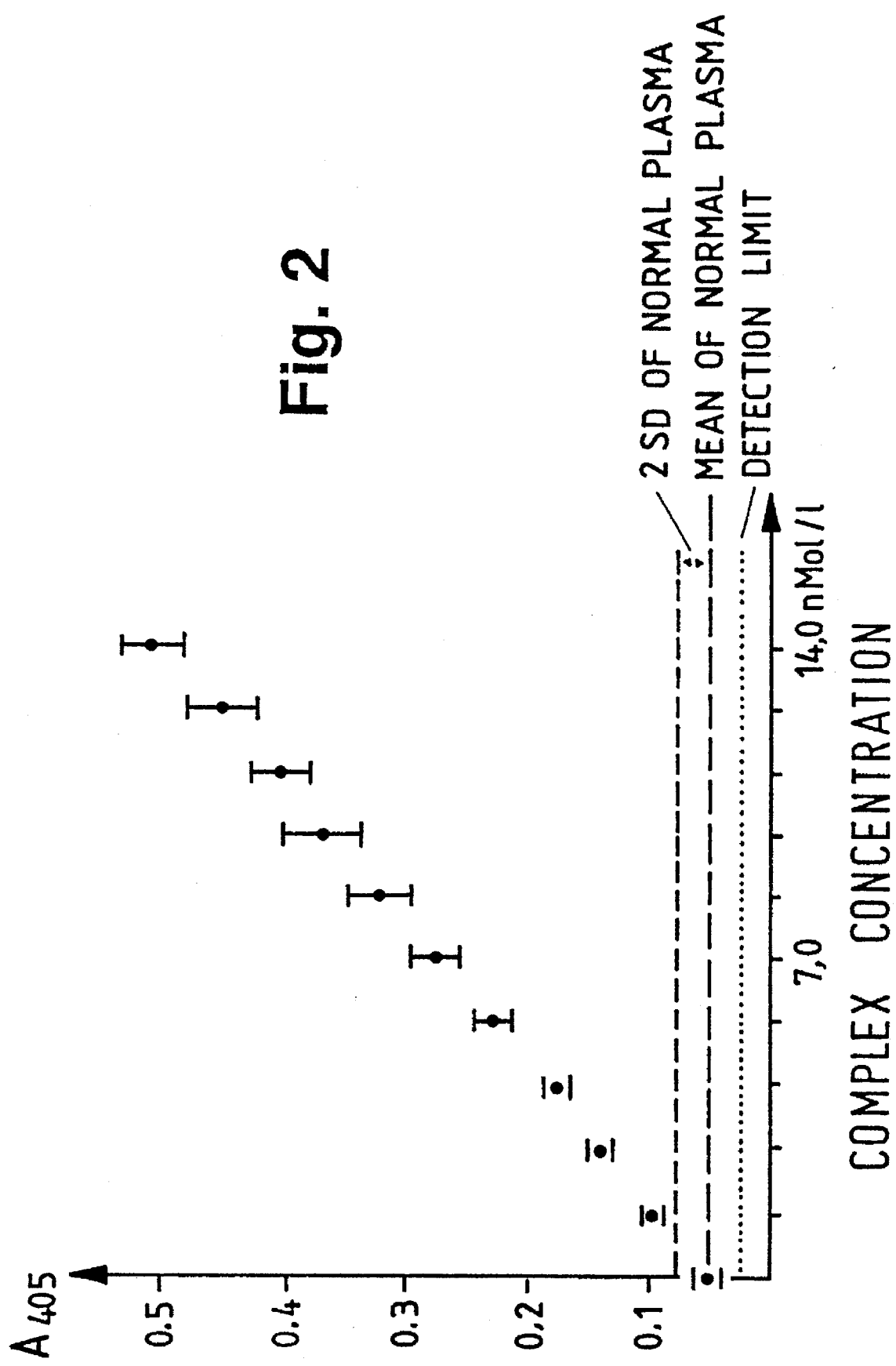
FIG. 2 shows a calibration series of normal pool plasma with up to 14 nMol/L of preformed complexes of α-1-antichymotrypsin added to this plasma.

Working range and calibration: A calibration series of normal pool plasma with up to 14 nMol/L of preformed complexes added was prepared (FIG. 2). After preliminary measurements, this range was chosen since it covered most of the values of patient specimens collected at random from several critically ill patients on an intensive-care unit (Table 1). Samples with absorption values exceeding those of the calibration series were diluted with normal pool plasma. Since no true sample blank was available, the lowest value of the calibration series, i.e. the value of normal pool plasma, was taken as reference. Therefore, concentrations derived from the calibration curve actually mean concentrations in addition to the complex concentration prevalent in the normal pool plasma. The absorbance from normal pool plasma was less than 10% increment of the calibration series (FIG. 2).

Time dependence and practicability: The assay will work if incubation times are shortened to 30 min per step, albeit with lower absolute absorbance readings. The minimum time between sample presentation and read-out will then amount to approximately 3.5 hours. However, the maximum amount of samples (6 microtiter plates) in one assay can only be measured if 60 minute incubations are used as specified in the description for the optimized assay, allowing 10 min for the handling of 1 plate in each step. To obtain comparable absolute absorbance readings, it is recommended to always use the full incubation times.

The inventive process can be employed in states of disease where liberation of cathepsin G and increased turn-over of α-1-anti-chymotrypsin may be suspected. In e.g. acute phase reactions it may give clues about the severity of the process whether the reaction is still being triggered or already dissolving since complexed α-1-antichymotrypsin sets a positive feedback signal in the acute phase reaction via interleukin-6 and is rapidly cleared from the circulation. Furthermore, this assay is helpful in gaining further insight into the physiological function of this prominent proteinase inhibitor system.

TABLE 1

| Patient Nr. | Diagnosis | nMol/L |
|---|---|---|
| 1 | Septicemia | 13.3 |
| 2 | Septicemia | 10.8 |
| 3 | Septicemia | 6.5 |
| 4 | Septicemia | 3.2 |
| 5 | Pancreas Transplant Rejection | 2.9 |
| 6 | Aspiration pneumonia | 2.7 |
| 7 | Bacterial Meningitis | 2.1 |
| 8 | Acute Bacterial Endocarditis | 2.0 |

Examples of plasma specimens of critically ill patients which had been used to choose the range of the calibration curve. Concentration of complexed alpha-1-antichymotrypsin in nMol/L.

EXAMPLE 1

Performance of the Inventive Process

Step 1. Coating with Albumin

Bovine serum albumin (BSA) was dissolved at 1% in phosphate-buffered saline (PBS), containing 0.05% TWEEN 20 (polysorbate) and 0.02% NaN3 (PBS-TWEEN); i.e., phosphate buffered saline containing polysorbate; 200 uL was added to each well and incubated for 60 min at 37° C. For all incubations mentioned in this assay, microtiter plates were kept in a moist atmosphere. Following incubation, wells were emptied by decantation and washed four times with 250 uL PBS-TWEEN, each washing cycle lasting 30 seconds. This washing procedure was used after all the followings steps as indicated by "washing".

Step 2. Sample Application

Plasma samples of 10 uL were added to 500 uL PBS-TWEEN containing 100 U/L heparin (Liquemin$^R$) and vortexed for 6 seconds. Immediately, 4 specimens of 100 ul each were then applied to 4 wells of the microtiter plate. For the calibration series, plasma from a healthy donor pool to which 14 nMol/L of preformed complex had been added, was diluted with the native plasma to prepare a series of calibration specimens down to 1.4 nMol/L in 10 equal increments. Blanks consisted of PBS-TWEEN (i.e., phosphate buffered saline containing polysorbate) only. Calibration samples for 1.4 nMol/L, 7.0 nMol/L, and 14 nMol/L were applied to each additional microtiter plate per run in duplicate. In order to keep the time necessary for the application of the diluted specimens to a minimum, they were arranged in a panel of Eppendorf cups matching the order as desired in the microtiter plate, so that fast transfer with a multichannel pipette was possible. Incubation was 60 min at 37° C., followed by the washing procedure.

Step 4. First Antibody Reaction

Rabbit-anti-human-α-1-antichymotrypsin antiserum was diluted 1:1000 in PBS-TWEEN (polysorbate) (i.e., phosphate buffered saline containing polysorbate) containing 1% BSA. 100 uL were applied to each well. Incubation was 60 min at 37° C., followed by the washing procedure.

Step 5. Second Antibody Reaction

Goat-anti-rabbit-IgG antiserum coupled to alkaline phosphatase was diluted 1:1000 in PBS-TWEEN (polysorbate) containing 1% BSA. 100 uL were applied to each well. Incubation was 60 min at 37° C., followed by the washing procedure.

Step 6. Developing

Alkaline phosphatase was detected by incubation with 100 uL/well of 4 g/L 4-nitrophenylphosphate in 0.1 mol/L glycine, pH 10.5, containing 0.01 mol/L MgCl2, at 37° C. for 30 min. Absorbance was measured at 405 nm.

Step 7. Calculation

Specimen absorbance was compared with the linear calibration curve, from which the concentration of complex above the normal level could be determined directly.

EXAMPLE 2

Precision of the process: Precision of the assay was estimated by measuring three specimens with low (1.9 nmol/L), medium (9.8 nmol/L), and high (14.0 nmol/L) concentrations of complexed α-1-antichymotrypsin. Six identical measurements were taken. The within-run coefficients of variation (CV) were 3.9%, 7.5% and 2.6%, the between-run CVs 5%, 4%, and 3%, respectively.

EXAMPLE 3

Accuracy: Addition of preformed complexes to normal pool plasma gave a linear increase in absorbance within the range of the assay (FIG. 2). Inactivation of cathepsin G with DFP prior to exposure to α-1-antichymotrypsin completely abolished the additional absorbance in the assay. Also, addition of DFP-inactivated cathepsin G directly to plasma did not generate a detectable absorbance signal. In 3 recovery experiments, 5 nmol/L of preformed complex was added to different specimens. The divergence between the expected and the actual absorbance (recovery) was below 10%.

EXAMPLE 4

Specificity of the process: When α-1-antichymotrypsin in a twofold molar excess was exposed to 14 nmol/L of bovine α-chymotrypsin or human leukocyte elastase instead of cathepsin G, no increased absorbance reading was generated. Extremely high additions of heparin to the specimens (250 U/ml and higher) resulted in a decrease of absorbance up to 30%, while lower concentrations (20 U/ml and lower) led to only marginal changes of absorbance (less than 5%). However, since many critically ill patients receive therapeutical doses of heparin, it was decided to add heparin to the specimen buffer at 100 U/L, corresponding to a plasma concentration of 5000 U/L, concentration high enough to render any heparin present in patients specimens irrelevant without significant deterioration of analytical capacity. Gross mechanical hemolysis in the specimens prior to centrifugation increased the absorbance signal up to 100%. Samples with signs of hemolysis should therefore not be included in this assay.

EXAMPLE 5

Detectability and reference range: The pooled plasma of 50 healthy individuals was taken (22 females, 28 males, ages 21 to 55 years) as reference. To estimate the concentration of complexes prevalent in the normal plasma, the calibration curve was used to extrapolate from the pooled normal plasma to the reagent blank. Measuring these plasmas individually, a mean value equivalent to 1.73 nmol/L was found, with a standard deviation of 0.58 nmol/L. Values exceeding the mean plus 2×standard deviation (2.89 nmol/L) were regarded as elevated. The detection limit, defined by the International Federation of Clinical Chemistry as the mean value of blank plus 2.6×standard deviation was 0.84 nmol/L.

We claim:

1. A process for detecting complexes of α-1-antichymotrypsin and cathepsin G in a sample, comprising:

(a) providing a solid phase wherein surface of the solid phase is saturated with a coating capable of adsorbing said cathepsin G but not said α-1-antichymotrypsin and wherein said coating is selected from the group consisting of a non-specific binding protein and gelatin;

(b) contacting the sample to the solid phase of step (a) to adsorb said complexes;

(c) contacting the solid phase of step (b) with an antibody which specifically binds to the α-1-antichymotrypsin present in the adsorbed complexes; and, (d) detecting bound antibody to detect the complexes in the sample.

2. The process according to claim 1 wherein the sample is selected from the group consisting of blood, plasma, serum, urine, saliva, synovial fluid, cerebrospinal fluid, bronchial lavage fluid and a cell culture supernatant.

3. The process according to claim 1 wherein the solid phase is selected from the group consisting of polystyrene, gold, silica, polyacrylamide and glass.

4. The process according to claim 1 wherein the solid phase is coated with said non-specific binding protein.

5. The process according to claim 4 wherein said non-specific binding protein is selected from the group consisting of bovine serum albumin and ovalbumin.

6. The process according to claim 1 wherein the antibody is a labeled polyclonal antibody or a labeled monoclonal antibody.

7. The process according to claim 6 wherein the antibody is labeled with a radioactive isotope, an enzyme, biotin, a chemiluminescent agent or a fluorescent agent.

8. The process according to claim 1 wherein the antibody is a first unlabeled antibody which is detected by a second labeled antibody which specifically binds to the first unlabeled antibody.

9. The process according to claim 8 wherein the second labeled antibody is a polyclonal antibody or a monoclonal antibody labeled with a radioactive isotope, biotin, a chemiluminescent agent, a fluorescent agent or an enzyme.

10. The process according to claim 9 wherein the enzyme is alkaline phosphatase or horseradish peroxidase.

11. A process for quantitating the amount of complexes of α-1-antichymotrypsin and cathepsin G in a sample, comprising:

(a) providing a solid phase wherein surface of the solid phase is saturated with a coating capable of adsorbing said cathepsin G but not said α-1-antichymotrypsin and wherein said coating is selected from the group consisting of a non-specific binding protein and gelatin;

(b) contacting the sample to the solid phase of step (a) to adsorb said complexes;

(c) contacting the solid phase of step (b) with an antibody which specifically binds to the α-1-antichymotrypsin present in the adsorbed complexes;

(d) measuring the amount of antibody bound to the solid phase of step (c); and, (e) determining the amount of said complexes in the sample by comparing the amount of bound antibody measured in step (d) with a calibration curve constructed by measuring the amount of bound antibody produced by calibrators comprising known quantities of said complexes assayed according to steps (a) through (d).

* * * * *